United States Patent [19]

Cooper

[11] Patent Number: 4,640,820
[45] Date of Patent: Feb. 3, 1987

[54] FLOW-THROUGH HOUSING WITH BLOOD GAS SENSORS

[75] Inventor: Robert P. Cooper, Yorba Linda, Calif.

[73] Assignee: Cardiovascular Devices, Inc., Irvine, Calif.

[21] Appl. No.: 546,493

[22] Filed: Oct. 28, 1983

[51] Int. Cl.$^4$ .................. G01N 21/05; G01N 33/48
[52] U.S. Cl. .................................. 422/68; 210/232; 210/445; 436/68
[58] Field of Search .................. 422/101, 81, 82, 48, 422/68; 436/178, 68; 210/433.2, 445, 451, 453, 321.1, 232, 335, 339

[56] References Cited

U.S. PATENT DOCUMENTS

| | | | |
|---|---|---|---|
| 3,907,687 | 9/1975 | Hoeltzenbein | 210/321.3 |
| 3,977,976 | 8/1976 | Spaan et al. | 210/321.4 |
| 3,980,564 | 9/1976 | Bardin et al. | 210/321.1 |
| 4,003,707 | 1/1977 | Lubbers et al. | 436/172 |
| 4,038,191 | 7/1977 | Davis et al. | 210/321 B |
| 4,184,962 | 1/1980 | Oscarsson et al. | 210/232 |
| 4,404,100 | 9/1983 | Mikhail | 210/232 |
| 4,415,447 | 11/1983 | Foucras et al. | 210/321.1 |

OTHER PUBLICATIONS

Siggaard-Andersen; The Acid-Base Status of the Blood, The Williams & Williams Co. 1974, p. 178.

Primary Examiner—Barry S. Richman
Assistant Examiner—Michael S. Gzybowski
Attorney, Agent, or Firm—Gordon L. Peterson

[57] ABSTRACT

An apparatus for sensing characteristics of a substance, such as blood, including a membrane support having first and second recesses and first and second dissimilar membranes extending over the first and second recesses, respectively. The membrane support has a groove between the recesses, and edge portions of the membranes extend into the groove on the side thereof adjacent the first recess. A retaining bar is received within the groove, and the membranes are tightly held between the retaining bar and the wall of the groove to form a smooth, essentially continuous surface. The membrane support forms a portion of a flow passage so that blood can flow along the membranes. First and second sensors are mounted on the sides of the first and second membranes opposite the flow passage for sensing characteristics of the blood. The first and second sensors engage the first and second membranes, respectively, to tension the membranes.

18 Claims, 5 Drawing Figures

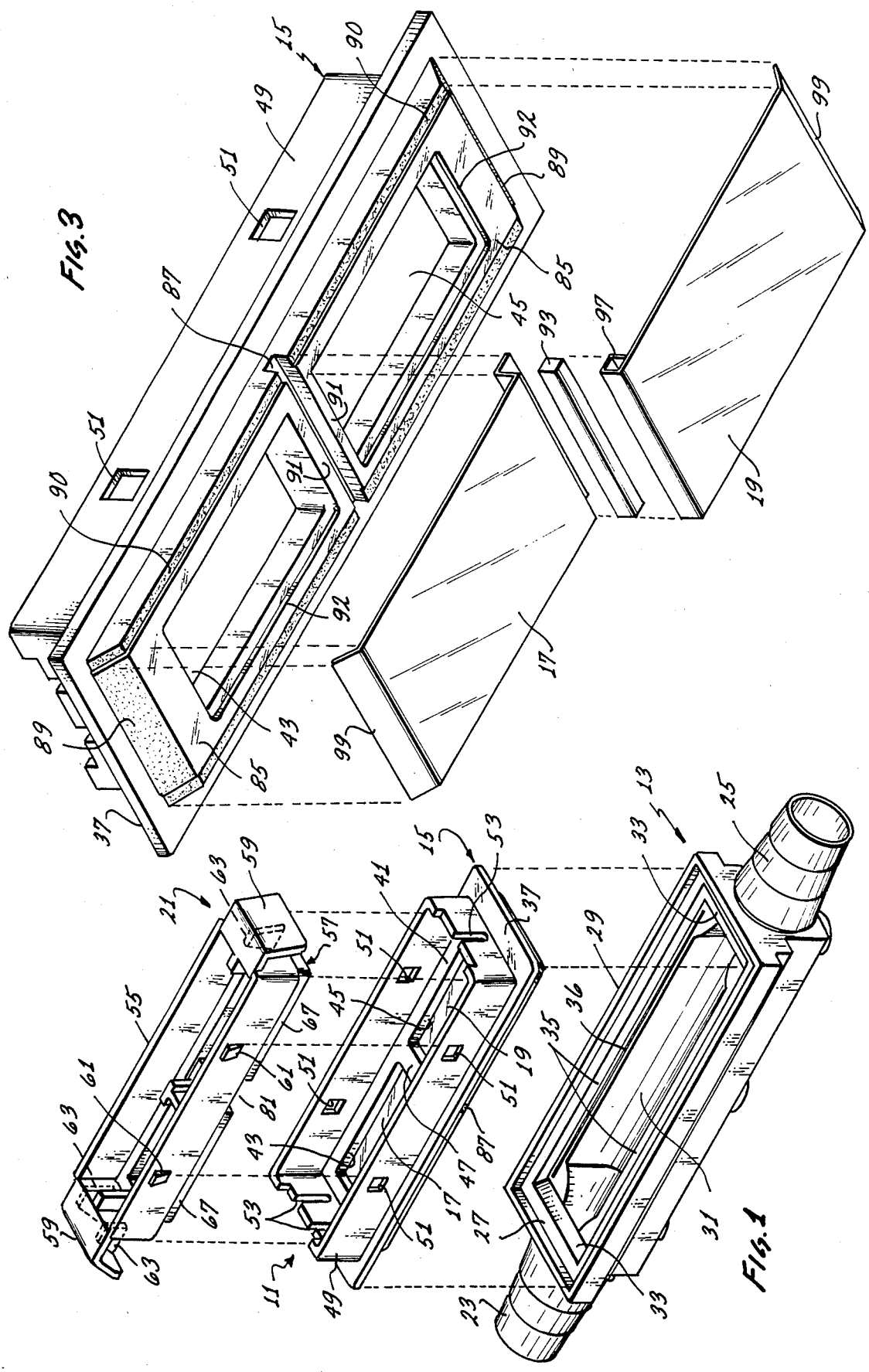

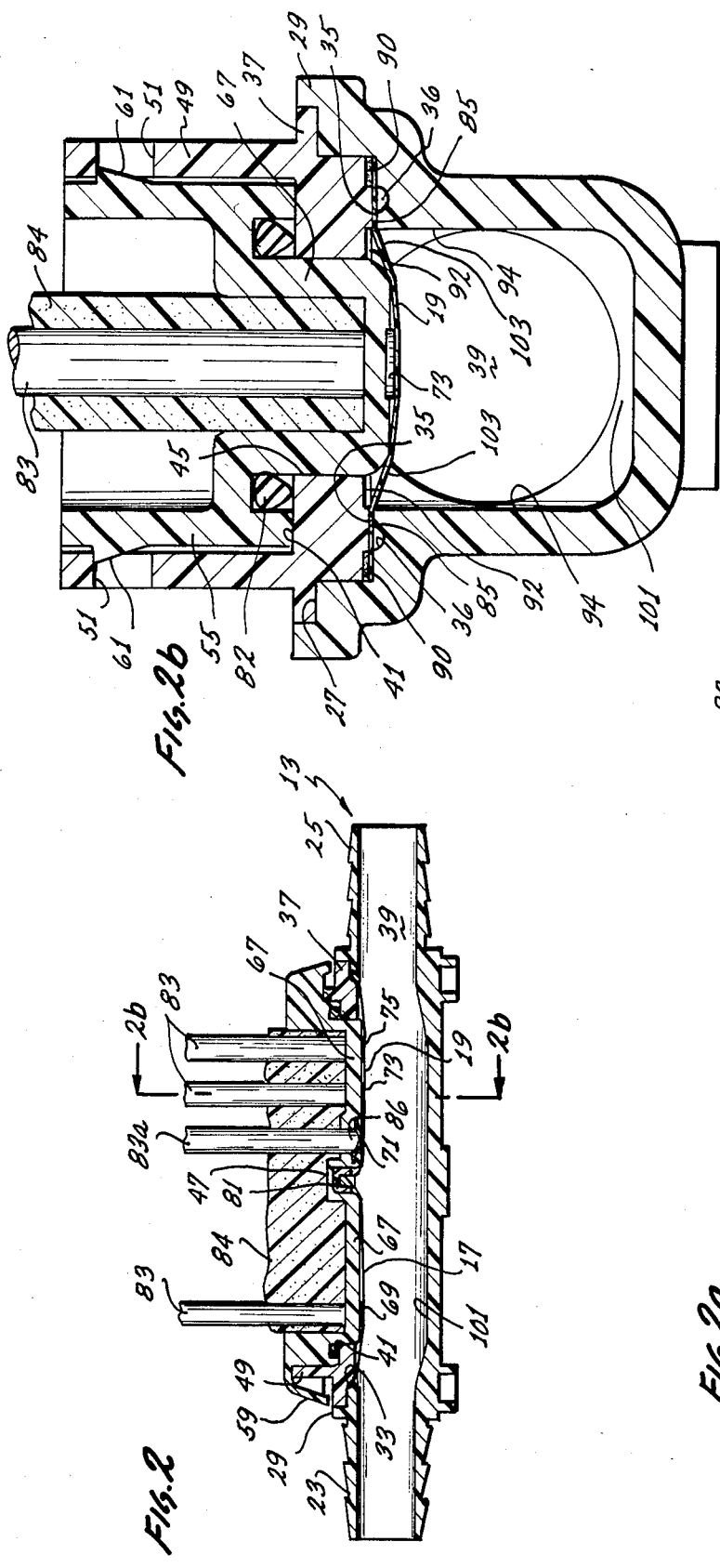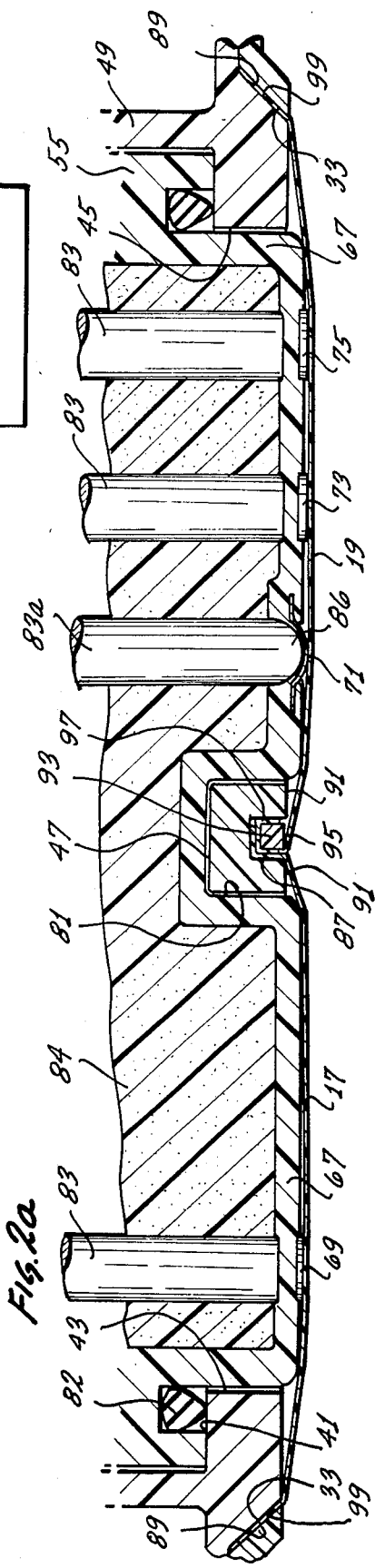

FLOW-THROUGH HOUSING WITH BLOOD GAS SENSORS

BACKGROUND OF THE INVENTION

It is sometimes necessary or desirable to know the partial pressure of certain blood gases and the pH of the blood. One way to accomplish this is to utilize a flow-through housing in an extracorporeal blood loop. In a system of this type, blood flows through the flow-through housing in such a manner as to enable the partial pressures of the blood gases and the pH to be determined.

More specifically, the housing includes two or more dissimilar membranes which allow appropriate components of the blood to pass through the membrane while excluding other components of the blood. The membranes must be dissimilar because each of them must pass and/or exclude different blood components in order that various different blood conditions can be sensed by sensors located at the sides of the membranes not exposed to the blood. For example, one of the membranes may pass oxygen and/or carbon dioxide but will not pass the liquid component of the blood. A second membrane passes an aqueous phase blood component that enables pH to be determined and creates a sterile barrier between the blood and the sensor system.

The blood components that pass through the two membranes are sensed by sensors to provide an indication of pH and the partial pressures of the applicable gases. One technique for accomplishing this is shown in Lubbers et al U.S. Pat. No. 4,003,707.

Although a system of this type performs very well, problems are presented by the mounting of two dissimilar membranes on a membrane support of the housing. If the dissimilar membranes are adhered to the membrane support in end-to-end relationship, the end portions tend to delaminate. This creates turbulence in the blood, tends to rupture the blood cells and to break the sterility barrier. Similar problems exist if the end portions of the dissimilar membranes are overlapped to form a lap joint. In addition, a lap joint, even without delamination, provides an undesirable, rough, nonuniform surface at the membrane interface, and it may be difficult or impossible to find an adhesive which will adhere two membranes of different materials together.

Another problem with the mounting of membranes on a membrane support is in making the membranes taut. This, of course, requires a secure attachment of the membrane to the membrane support so that the membrane can be pulled tightly. Unfortunately, some membranes tend to elongate when wet, and consequently, a membrane of this type may be taut in the initial dry state and relatively loose in a wetted condition. A loose membrane is undesirable because it ripples as liquid flows past the membrane, and this creates erratic results and prevents the membrane from lying flat on the surface of the sensor during operation.

SUMMARY OF THE INVENTION

This invention overcomes these problems by providing a secure attachment of dissimilar membranes in a flow-through housing so as to substantially prevent delamination at the joint and the accompanying problems. This invention also provides a smooth transition between the membranes, and the membranes are tensioned so that they remain taut when in use even when exposed to a liquid.

Although the attachment features of this invention are applicable to the attachment of similar or dissimilar membranes to a membrane support, they are particularly adapted for the attachment of dissimilar membranes. Dissimilar membranes are membranes having at least one meaningful difference, such as differences in materials, thicknesses and components which will pass through the membrane. Similarly, the attachment features of this invention are applicable to the attachment of only a single membrane to the membrane support.

This invention provides an apparatus which comprises a membrane support having first and second recesses, first and second membranes extending over the first and second recesses, respectively, and means for mounting the first and second membranes on the membrane support with the membranes extending over the first and second recesses, respectively. According to this invention, the mounting means includes groove means between the recesses. Edge portions of the membranes extend into the groove means. The mounting means also includes means for retaining the edge portions of the membranes in the groove means. This provides a strong attachment near the juncture of the two membranes so that the membranes can be pulled tightly across their respective recesses and adhered, or otherwise secured, to other locations on the membrane support.

Preferably, the groove means includes a groove and the edge portions of the membrane extend into the groove on the side thereof adjacent the first recess. To provide a smooth, uniform joint between the membranes, the second membrane extends over the retaining means on the side thereof facing outwardly of the groove and then extends into the groove. This also strengthens the attachment of the membranes to the membrane support and minimizes the exposure of foreign surfaces to the blood. To further enhance smoothness near the joint, the side of the retaining means facing outwardly of the groove is preferably generally flat, and the membrane support has first and second generally flat surfaces between the groove and the recesses which are generally coplanar with such side of the retaining means.

Although the retaining means can take different forms, it preferably includes a retaining bar. The retaining bar and the groove are sized so that the membranes are tightly held between the retaining bar and the wall of the groove. By wrapping the edge portions of the membrane at least part way around the retaining bar, a strong mechanical lock is formed. This mechanical lock is preferably supplemented by adhesive. In a preferred construction, the groove and the retaining bar are of rectangular cross section, and for a joint of maximum strength, at least one of the edge portions of the membranes is wrapped at least 270 degrees around the retaining bar. If membranes that can be bonded on only one side are used, then a region of the end portion of the second membrane preferably extends beyond the end portion of the first membrane within the groove.

Although the features of this invention are applicable to static conditions in which there is no flow past the membrane, they are particularly adapted for use with a flow-through housing in which blood, or other liquid, flows along the membrane. For this purpose, the apparatus may include wall means defining a passage for the flow of liquid therethrough. The wall means includes the membrane support. With this construction, the recesses are separated from the passage by the membranes.

The first and second membranes are permeable to at least first and second components of the liquid flowing through the housing. First and second sensors are mounted on the sensor support for sensing a characteristic of the first and second components, respectively. To further tension the membranes, means, which may include the first and second sensors, the sensor mounting structure, and/or other structure, projects through the recesses and engages the first and second membranes, respectively, on the sides thereof opposite the passage and tensions the membranes so engaged. Accordingly, the membranes will not ripple even when wet. In addition, if the sensors engage the associated membranes, there is no tendency to trap bubbles between the sensors and the membranes. Finally, the time constant of the system can be shortened by placing the sensors in intimate contact with the associated membrane.

The tensioning of the membranes causes them to project into the flow passage slightly. To at least partly compensate for this, the wall of the flow passage has an appropriately sized channel.

The tensioning of the membranes requires a strong attachment between the membranes and the membrane support and, for this reason, is particularly adapted for use with the membrane mounting technique of this invention. However, the use of the sensors to tension the membranes can be used with other forms of attachment for the membranes to the membrane support.

The invention, together with additional features and advantages thereof, may best be understood by reference to the following description taken in connection with the accompanying illustrative drawing.

BRIEF DESCRIPTION OF THE DRAWING

FIG. 1 is an exploded isometric view of a flow-through housing constructed in accordance with the teachings of this invention.

FIG. 2 is a longitudinal sectional view through the flow-through housing.

FIG. 2a is an enlarged fragmentary sectional view of a portion of FIG. 2 illustrating the tensioning of one of the membranes.

FIG. 2b is an enlarged sectional view taken generally along line 2b—2b of FIG. 2.

FIG. 3 is an exploded isometric view of the membrane support and the membranes.

DESCRIPTION OF THE PREFERRED EMBODIMENT

FIG. 1 shows an apparatus in the form of a flow through housing assembly 11 which generally comprises a housing section 13, a membrane support 15, membranes 17 and 19 and a sensor support 21. The housing section 13, the membrane support 15 and the sensor support 21 may each be constructed of a suitable plastic material, such as polycarbonate.

The housing section 13, which may be integrally molded, is hollow and has an inlet 23 and an outlet 25 for coupling the housing assembly 11 into an extracorporeal blood loop. The housing 13 has an annular, rectangular ledge 27 facing upwardly adjacent its upper end and an annular rectangular flange 29 projecting upwardly from the ledge and surrounding the ledge to define an opening 31 in the upper end of the housing section 13. Ramp surfaces 33 are provided at the opposite ends of the housing section 13, and longitudinal ledges 35 extend longitudinally from the lower ends of the ramp surfaces 33. Longitudinal grooves 36 (FIG. 2b) are provided in the ledges 35 to catch adhesive used in assembly and keep it out of the blood flow path.

The membrane support 15, which may be integrally molded, has a peripheral flange 37 sized to be received within the flnage 29 and to rest on the ledge 27 of the housing section 13 as shown in FIG. 2. The membrane support 15 may be adhered to, or otherwise suitably attached to, the housing section 13. When so attached, the housing section 13 and the membrane support 15 provide wall means defining a flow passage 39 which extends longitudinally through the housing from the inlet 23 to the outlet 25. Flow through the flow passage 39 can be in either direction.

The membrane support 15 has a lower wall 41 with recesses in the form of rectangular openings 43 and 45. A web 47 of the wall 41 extends between the openings. The membranes 17 and 19 extend completely across and cover the openings 43 and 45 so that the openings are separated from the passage 39 by the membranes. The membrane support 15 has an upstanding circumscribing wall 49 which has attachment apertures 51 in its longitudinal portions and orientation slots 53 in its end walls.

The sensor support 21 comprises a peripheral wall 55 extending upwardly from a base 57. Tabs 59 are attached to the opposite ends of the peripheral wall 55. The peripheral wall 55 has lugs 61 adapted to be received within the apertures 51, respectively, and locator lugs 63 adapted to be received within the slots 53, respectively. The lugs 61 can be resiliently deflected toward each other to permit the lugs 61 to enter the apertures 51 to securely mount the sensor support 21 on the membrane support 15. For shipment and storage, a removable safety plug (not shown) is mounted on the membrane support 15 in place of the sensor support 21.

The base 57 includes optically transparent dished sections 67 carrying sensors 69, 73, and 75 and a sensor receiver 71 of metal having high thermal conductivity. The dished sections are separated by a space 81 which is adapted to receive the web 47 as shown in FIG. 2. Also as shown in FIG. 2a, in the assembled condition, the wall 41 supports an annular region of the base 57 of the sensor support 21, and an annular seal 82 (FIGS. 2a and 2b) seals the interface with the membrane support 15.

The sensors 69, 73, and 75 are selected to sense a characteristic of the liquid flowing through the passage 39. Although various different characteristics can be sensed in this embodiment of the invention, the sensor 69 senses the partial pressure of oxygen, the sensor receiver 71 receives a thermistor 86 which senses temperature, the sensor 75 senses the partial pressure of carbon dioxide, and the sensor 73 senses pH. Although sensing can be accomplished in many different ways, in this embodiment, it is accomplished optically using fluorescent techniques as described, for example, in Lubbers et al U.S. Pat. No. 4,003,707 and Heitzmann U.S. Pat. application Ser. No. 425,420 filed on Sept. 28, 1982. For this purpose, optical fibers 83 are suitably coupled to the sensor support 21 for the purpose of conducting light to and from the respective sensors 69, 73 and 75, and wires 83a are coupled to the thermistor in the sensor receiver 71. The optical fibers 83, wires 83a and the thermistor are suitably releasably retained in the sensor support 21 by a molded retainer 84.

The membranes 17 and 19 must be selected so as to pass a component of the liquid, such as blood, which is to be measured. For example, in this embodiment, the membrane 17 is constructed of polytetrafluoroethylene, passes oxygen and serves as a halothane gas and liquid barrier. The membrane 19 is a microporous membrane that serves as a sterility barrier and passes virtually all blood components of interest, except bacteria. Specifically, aqueous phase materials, including dissolved carbon dioxide and hydrogen ions, are passed. This permits the partial pressure of carbon dioxide and the hydrogen ion concentration to be sensed in accordance with known techniques. One suitable material for the membrane 19 is a polyvinylidene fluoride which is available from Millipore under the trademark Durapore.

As best shown in FIG. 3, the membrane support 15 has coplanar, annular, rectangular surfaces 85 surrounding the openings 43 and 45, respectively, and a groove 87 of rectangular cross-sectional configuration evenly spaced between the openings 43 and 45. Ramp surfaces 89 slope upwardly from the opposite ends of the two coplanar surfaces 85. The groove 87 is spaced from the openings 43 and 45 by flat, coplanar surfaces 91 which form portions of the surfaces 85, respectively. Longitudinal grooves or recesses 90 extend along the opposite outer longitudinal edges of the surfaces 85 and the ramp surfaces 89, and grooves or recesses 92 extend along three of the inner edges of the surfaces 85, i.e., along all of the such inner edges, except the inner edge adjacent the surface 91. The outer edge of the longitudinal portion of each of the grooves 92 is coplanar with an inner surface 94 of the housing section 13 (FIG. 2b).

The membranes 17 and 19 are retained on the membrane support 15 by retaining means which includes a retaining bar 93 and adhesive. As shown in FIG. 2a, edge portions of the membrane extend into the groove 87 on the side of the groove adjacent the opening 43. The membrane 19 is wrapped almost completely around the retaining bar 93 and the membrane 17 extends along two sides of the retaining bar outside of the membrane 19. The retaining bar 93 has a flat face 95 facing outwardly of the groove, and the membrane 19 extends over the flat face 95 and then into the groove 87 to thereby form a smooth transition between the membranes 17 and 19. A region 97 of the end portion of the membrane 19 extends beyond the end portion of the membrane 17 within the groove 87 and is adhered to the wall of the groove. This provides a stronger construction and allows the region 97 to be directly adhered to the membrane support 15 even if only one face of the membrane 19 is capable of being adhesively attached.

The retaining bar 93 is sized and configured relative to the groove 87 so that the membranes 17 and 19 are tightly held between the retaining bar and the wall of the groove. This forms a mechanical lock which mechanically locks the end portions of the membranes 17 and 19 to the membrane support 15. In the embodiment illustrated, the retaining bar 93 is rectangular, and while this configuration is preferred, it is not essential. The vertical dimension of the retaining bar 93 as viewed in FIG. 2a is such as to place the face 95 essentially coplanar with the surfaces 91 so as to maintain the membranes 17 and 19 essentially coplanar and to provide a smooth transition between them. Adhesive is applied between the end portions of the membranes 17 and 19 and between such end portions and the walls of the groove 87 to create both a seal and a bond.

Peripheral regions of the membranes 17 and 19 are adhered to the surfaces of the groove 90, and outer end portions 99 of the membranes are adhered to the ramp surfaces 89. The membranes 17 and 19 are sized to completely cover their respective openings 43 and 45 and to be essentially coextensive with the surfaces 85, the bottom surface of the grooves 90 and the ramp surfaces 89.

During assembly, adhesive is first applied to both sides of the adjacent end portions of the membranes 17 and 19 and they are positioned in the groove 87, with the region 97 extending beyond the end portion of the membrane 17. Adhesive is applied to the retaining bar 93, and the retaining bar is forced into the groove 87 to the position shown in FIG. 2a. The membranes 17 and 19 can then be pulled tightly outwardly away from the bar 93 and adhered to the surfaces of the grooves 90 and the ramp surfaces 89. Because of the strong attachment between the confronting end portions of the membranes 17 and 19 and the membrane support 15, the membranes can be placed under a significant tensile load and tightly stretched over the openings 43 and 45.

With the membrane support mounted on the housing section 13, the longitudinal edge portions of the membranes 17 and 19 are clamped between the surfaces 85 of the membrane support 15 and the ledges 35 of the housing section (FIG. 2b). With the sensor support 21 received within, and mounted on, the membrane support 15 as shown in FIG. 2, the sensors 69, 73 and 75, as well as the receiver 71, and the dished sections 67 engage the membranes 17 and 19 along longitudinally extending regions of the membranes and force them downwardly slightly as viewed in FIGS. 2a and 2b to further tension the membranes. The desired amount of the downward distension of the membranes 17 and 19 depends upon the tendency of the membranes to distend when wet and, in this embodiment, may be, for example, about 0.030 to 0.060 inch. This distension provides for tight engagement between the sensors and the thermistor receiver 71 and the associated membranes so as to reduce the likelihood of trapping bubbles between the sensors and the thermistor receiver and the membranes, to reduce the time constant of the system, to increase thermal conductivity to the thermistor receiver, and to cause the membrane to lie flat against the sensors and the thermistor receiver. The distension does not provide an unacceptable discontinuity for blood flow across the membranes. However, the housing section 13 has a longitudinal channel 101 below the distended regions of the membranes to approximately compensate for the projection of the membranes into the flow passage and keep the cross-sectional area of the flow passage 39 approximately constant. Of course, the distension is greatly exaggerated in the drawing for clarity. Because the membranes 17 and 19 are tensioned, they will not become loose and allowed to ripple even if they undergo some elongation as a result of becoming wet from the blood in the passage 39. Consequently, the membranes cannot ripple and produce erratic results for that reason.

The grooves 90 provide a space for the adhesive, and the grooves 92 provide a gap which prevents any adhesive that may leak inwardly from adhering the membranes 17 and 19 to the membrane support at that location. Consequently, the tensioning of the membranes 17 and 19 by the sensor support 21 can create an inclined section 103 (FIG. 2b) adjacent each longitudinal membrane edge which prevents the sensor support from shearing the membrane.

In use, the flow-through housing assembly 11 is coupled via the inlet 23 and the outlet 25 into an extracorporeal blood path so that the flow passage 39 forms part of the extracorporeal loop. Accordingly, the flow of blood along the membranes 17 and 19 is generally parallel to the plane of the membranes. The membranes 17 and 19 are semi-permeable and pass the blood components identified above and serve as a barrier for the other components of the blood. Consequently, the sensor 69 is exposed to oxygen, and the sensors 73 and 75 are exposed to dissolved carbon dioxide and hydrogen ions. Each of these sensors contains an appropriate indicator which permits the partial pressure of a particular blood gas or the hydrogen ion concentration to be optically determined in accordance with known techniques which form no part of this invention. Although the features of this invention relating to the mounting of the membranes 17 and 19 and the tensioning of these membranes are particularly adapted to the sensing of blood gases and hydrogen ion concentration, they are also applicable to many other systems.

Although an exemplary embodiment of the invention has been shown and described, many changes, modifications and substitutions may be made by one having ordinary skill in the art without necessarily departing from the spirit and scope of this invention.

I claim:

1. A membrane support apparatus comprising:
   a membrane support having first and second recesses;
   first and second membranes extending over the first and second recesses, respectively, said first and second membranes being permeable to at least a component of a liquid;
   means for mounting the first and second membranes on the membrane support with the membranes extending over the first and second recesses, respectively;
   said mounting means including a groove in the membrane support between the recesses, edge portions of said membranes extending into said groove;
   said mounting means including means for retaining the edge portions in said groove; and
   said edge portions of said first membrane extending into said groove on a side thereof adjacent the first recess, and said second membrane extending over said retaining means on a side thereof facing outwardly of said groove and then extending into said groove to thereby form a smooth transition with said first membrane.

2. An apparatus as defined in claim 1 wherein said groove is rectangular in cross section for receiving the end portion of the first membrane, and said retaining means includes a retaining bar of generally rectangular cross-sectional configuration receivable in said groove.

3. An apparatus as defined in claim 1 wherein said first and second membranes are permeable to at least first and second components of the liquid, respectively, and said apparatus includes first and second sensors for sensing a characteristic of the first and second components, respectively, said first and second sensors engaging the first and second membranes respectively, and tensioning the membranes so engaged, said first sensor engaging the first membrane on a side thereof that faces the first recess and said second sensor engaging the second membrane on a side thereof that faces the second recess.

4. An apparatus as defined in claim 1 including a sensor support, a sensor carried by the sensor support for sensing a characteristic of said component of the liquid, and means for mounting the sensor support on the membrane support with said sensor being on a side of one of said membranes which faces the recess which said one membrane extends over.

5. An apparatus as defined in claim 1 including wall means defining a passage for flow of the liquid therethrough, said wall means including said membrane support, said membranes being dissimilar and said first and second recesses being separated from the passage by the first and second membranes, respectively.

6. An apparatus as defined in claim 5 wherein said second membrane is wrapped around at least 270 degrees of the retaining means.

7. An apparatus as defined in claim 5 wherein said retaining means includes a retaining bar and said edge portions of said membranes are tightly held between the retaining bar and a surface of the groove.

8. An apparatus as defined in claim 5 wherein a region of the edge portion of the second membrane extends beyond the edge portion of the first membrane within said groove and said region is adhered to a surface of the groove.

9. An apparatus as defined in claim 5 wherein said groove is rectangular in cross section, said retaining means includes a retaining bar of generally rectangular cross section a face of the retaining bar facing the passage, said membrane support has first and second generally flat surfaces between the groove and the first and second recesses, respectively, which are generally coplanar with said face of the bar, said edge portion of the second membrane extends at least partially around four faces of the rectangular retaining bar, a region of the edge portion of the second membrane extends beyond the edge portion of the first membrane within said groove and is adhered to a surface of the groove.

10. An apparatus as defined in claim 5 including means on the membrane support extending through at least one of said recesses for engaging and tensioning the membrane which extends over said at least one recess.

11. An apparatus as defined in claim 1 wherein the membrane support has first and second surfaces surrounding the first and second recesses, respectively, and longitudinal grooves extending along opposite longitudinal edges of the first and second surfaces, said mounting means includes adhesive in the longitudinal grooves adhering the membranes to the membrane support.

12. An apparatus as defined in claim 5 wherein one side of each of the membranes faces the passage and said apparatus includes a sensor support, first and second sensors carried by the sensor support for sensing first and second characteristics, respectively, of said component of the liquid, and means for mounting the sensor support on the membrane support with the first and second sensors being adjacent the first and second membranes on sides thereof opposite to said passage.

13. An apparatus as defined in claim 5 wherein said retaining means has a side facing said passage which is generally flat.

14. An apparatus as defined in claim 13 wherein said membrane support has first and second generally flat surfaces between the groove and the first and second recesses, respectively, which are generally coplanar with said side of the retaining means.

15. An apparatus as defined in claim 5 wherein said first and second membranes are permeable to at least first and second components of the liquid, respectively, and said apparatus includes first and second sensors for sensing a characteristic of the first and second components, respectively, said first and second sensors engaging the first and second membranes, respectively, on sides thereof opposite said passage and tensioning the membranes so engaged.

16. An apparatus as defined in claim 15 wherein said groove is rectangular in cross section, said retaining means includes a retaining bar of generally rectangular cross section with a face of the retaining bar facing the passage, said membrane support has first and second generally flat surfaces between the groove and the first and second recesses, respectively, which are generally coplanar with said face of the bar, and said edge portions of said membranes are tightly held between the retaining bar and a surface of the groove.

17. A flow through apparatus comprising:
    wall means defining a passage for the flow of liquid therethrough, said wall means including a membrane support having a first recess;
    a first membrane extending over the first recess, said membrane being exposable to a liquid on one side thereof and being permeable to at least a component of the liquid;
    means for mounting the first membrane on the membrane support with the membrane extending over the recess;
    said mounting means including a groove in said membrane support adjacent one end of the recess and a retaining bar; and
    an edge portion of said membrane being wrapped at least part way around said retaining bar and extending over said retaining bar on a side thereof facing outwardly of said groove, said retaining bar and said edge portion being tightly received in said groove whereby the edge portion of the membrane is tightly held between the retaining bar and the wall of the groove.

18. An apparatus as defined in claim 17 including means on the membrane support extending through said first recess for engaging and tensioning the membrane.

* * * * *